US00PP15324P2

(12) United States Plant Patent
Smith

(10) Patent No.: US PP15,324 P2
(45) Date of Patent: Nov. 16, 2004

(54) ***CHRYSANTHEMUM* PLANT NAMED 'FESTIVE YOURSULA'**

(50) Latin Name: *Chrysanthemum×morifolium*
Varietal Denomination: Festive Yoursula

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/764,881

(22) Filed: Jan. 26, 2004

(51) Int. Cl.[7] ..... A01H 5/00

(52) U.S. Cl. ..... Plt./287

(58) Field of Search ..... Plt./287

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Festive Yoursula', characterized by its compact, upright and outwardly spreading plant habit; freely branching habit; dense and full plant habit; uniform and freely flowering habit; small decorative-type inflorescences with elongated oblong-shaped ray florets; bronze-colored ray florets; and natural season flowering in mid September in the Northern Hemisphere.

2 Drawing Sheets

Botanical classification/cultivar designation: *Chrysanthemum×morifolium* cultivar Festive Yoursula.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Festive Yoursula'.

The new cultivar is a product of a planned breeding program conducted by the Inventor in Alva, Fla. The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Yoursula, disclosed in U.S. Plant Pat. No. 13,641. The new *Chrysanthemum* was discovered and selected by the Inventor as a single flowering plant from within a population of plants of the cultivar Yoursula in a controlled environment in Alva, Fla. in April, 2002. The selection of this plant was based on its desirable inflorescence form, attractive ray floret color and good garden performance.

Asexual reproduction of the new cultivar by terminal vegetative cuttings in a controlled environment in Alva, Fla. since June, 2002, has shown that the unique features of this new *Chrysanthemum* are stable and reproduced true to type in successive generations.

SUMMARY OF THE INVENTION

The cultivar Festive Yoursula has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Festive Yoursula'. These characteristics in combination distinguish 'Festive Yoursula' as a new and distinct cultivar:

1. Compact, upright and outwardly spreading plant habit.
2. Freely branching habit; dense and full plants.
3. Uniform and freely flowering habit.
4. Small decorative-type inflorescences with elongated oblong-shaped ray florets.
5. Bronze-colored ray florets.
6. Natural season flowering in mid September in the Northern Hemisphere.

In side-by-side comparisons conducted in Alva, Fla., plants of the new *Chrysanthemum* differed from plants of the parent, the cultivar Yoursula, primarily in ray floret coloration as plants of the cultivar Yoursula had lavender-colored ray florets. In addition plants of the new *Chrysanthemum* flowered a couple of days later than plants of the cultivar Yoursula when grown under natural season conditions.

Plants of the new *Chrysanthemum* differ primarily from plants of the cultivar Sunny Yoursula, disclosed in a U.S. Plant patent application filed concurrently, in ray floret coloration.

Plants of the new *Chrysanthemum* can be compared to plants of the *Chrysanthemum* cultivar Robin, disclosed in U.S. Plant Pat. No. 8,300. In side-by-side comparisons conducted in Alva, Fla., plants of the new *Chrysanthemum* differed from plants of the cultivar Robin in the following characteristics:

1. Plants of the new *Chrysanthemum* were more rounded than plants of the cultivar Robin.
2. Plants of the new *Chrysanthemum* flowered five to seven days later than plants of the cultivar Robin when grown under natural season conditions.
3. Ray florets of plants of the new *Chrysanthemum* did not fade as quickly as ray florets of plants of the cultivar Robin.

Plants of the new *Chrysanthemum* can also be compared to plants of the *Chrysanthemum* cultivar Orange Urano, disclosed in U.S. Plant Pat. No. 13,019. In side-by-side comparisons conducted in Alva, Fla., plants of the new

*Chrysanthemum* differed from plants of the cultivar Orange Urano in the following characteristics:

1. Plants of the new *Chrysanthemum* were not as outwardly spreading as plants of the cultivar Orange Urano.
2. Plants of the new *Chrysanthemum* flowered about one week later than plants of the cultivar Orange Urano grown under natural season conditions.
3. Plants of the new *Chrysanthemum* had smaller inflorescences than plants of the cultivar Orange Urano.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproduction of this type. Colors in the photographs may differ slightly from the color values cited in the detailed botanical description which accurately describe the colors of the new *Chrysanthemum*.

The photograph on the first sheet comprises a side perspective view of a typical flowering plant of 'Festive Yoursula' grown in a container.

The photograph on the second sheet comprises a close-up view of typical inflorescences of the cultivar 'Festive Yoursula'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Alva, Fla. during the winter in a fiberglass-covered greenhouse under conditions and practices which approximate those generally used in commercial garden-type *Chrysanthemum* production. One cutting was planted in a 15.25-cm container in early December, 2002. Plants were pinched one time, that is, the terminal apex was removed to enhance branching, at the end of December. One week after the pinch, plants were exposed to short day/long night photoperiodic treatments until flowering. During the production of the plants, day temperatures averaged 26° C. and night averaged 18° C. Measurements and numerical values represent averages for typical flowering plants.

Botanical classification: *Chrysanthemum×morifolium* cultivar Festive Yoursula.

Commercial classification: Decorative-type garden *Chrysanthemum*.

Parentage: Naturally-occurring whole plant mutation of the *Chrysanthemum×morifolium* cultivar Yoursula, disclosed in U.S. Plant Pat. No. 13,641.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded crown; compact plant habit. Stems initially upright, then outwardly spreading. Freely branching with about nine lateral branches per plant. Moderately vigorous.

*Plant height.*—About 20 cm.

*Plant diameter.*—About 25 cm.

*Lateral branches.*—Length: About 17.5 cm. Diameter: About 3.25 mm. Internode length: About 9 mm. Aspect: Upright and outwardly spreading. Texture: Pubescent. Color: Close to 146A.

*Foliage description.*—Leaf arrangement: Alternate. Length: About 5.5 cm. Width: About 4.8 cm. Apex: Mucronate. Base: Attenuate with truncate tendencies. Margin: Palmately lobed, sinuses divergent to parallel. Texture, upper surface: Slightly pubescent. Texture, lower surface: Pubescent; veins prominent. Color: Developing and fully expanded foliage, upper surface: 147A. Developing and fully expanded foliage, lower surface: 147B. Venation, upper surface: 147A. Venation, lower surface: 147B. Petiole length: About 2 cm. Petiole diameter: About 2 mm. Petiole color, upper surface: 147B to 147C. Petiole color, lower surface: 147C.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. About 18 inflorescences per lateral branch.

*Flowering response.*—Under natural season conditions, plants flower in mid September in the Northern Hemisphere.

*Inflorescence bud (before showing color).*—Height: About 4 mm. Diameter: About 5 mm. Shape: Oblate. Color (lower surface of phyllaries): Darker than 146A.

*Inflorescence size.*—Diameter: About 2.9 cm; small. Depth (height): About 1 cm. Disc diameter: About 2 mm; inconspicuous. Receptacle diameter: About 3.5 mm.

*Ray florets.*—Shape: Elongated oblong. Length: About 1.3 cm. Corolla tube length: About 1 mm. Width: About 3.25 mm. Apex: Rounded or emarginate. Margin: Entire. Texture: Smooth, glabrous; satiny. Surface: Concave. Orientation: Initially upright, then perpendicular to vertical. Number of ray florets per inflorescence: About 82 in numerous whorls. Color: When opening, upper surface: Close to 9B to 9D overlain with 46A to 53A. When opening, lower surface: Close to 9C to 9D underlain with 46A to 53A. Fully opened, upper surface: Close to 9C to 9D faintly overlain with 46A to 53A. Fully opened, lower surface: Close to 9D faintly underlain with 46A to 53A.

*Disc florets.*—Shape: Tubular; apex dentate, five-pointed. Length: About 2.5 mm. Width, apex: About 1 mm. Width, base: About 1 mm. Number of disc florets per inflorescence: About 35. Color: Immature: Close to 154A. Mature: Apex: Close to 9A. Mid-section: Close to 144B. Base: Close to 155D.

*Phyllaries.*—Quantity per inflorescence: About 16. Length: About 6 mm. Width: About 2 mm. Shape: Lanceolate. Apex: Acute. Base: Truncate. Margin: Entire. Texture, upper surface: Smooth, waxy. Texture, lower surface: Pubescent. Color, upper surface: Close to 147A. Color, lower surface: Darker than 146A.

*Peduncle.*—Length: First peduncle: About 4 cm. Fourth peduncle: About 6.9 cm. Seventh peduncle: About 9.2 cm. Diameter: About 1 mm. Strength: Strong. Aspect: About 40 to 45° from vertical. Texture: Pubescent. Color: Close to 146A.

*Reproductive organs.*—Androecium: Present on disc florets only. Anther color: 9A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0 to more than 38° C.

It is claimed:

1. A new and distinct cultivar of *Chrysanthemum* plant named 'Festive Yoursula', as illustrated and described.

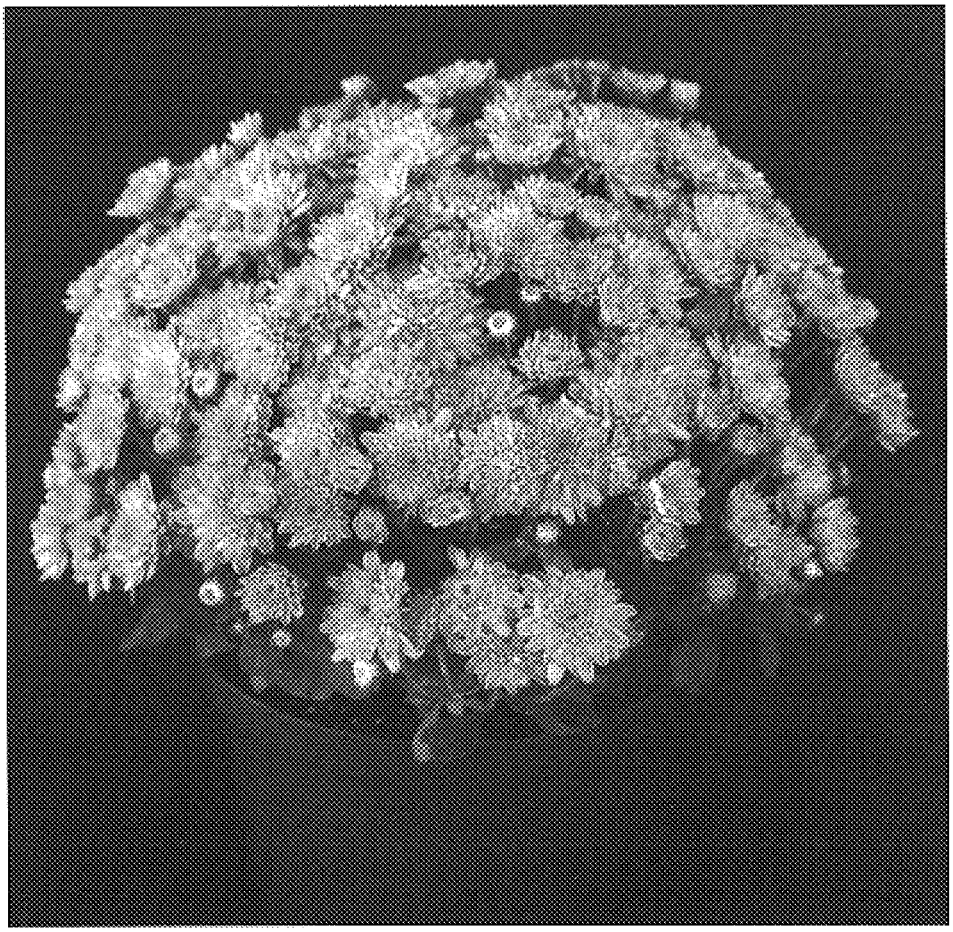

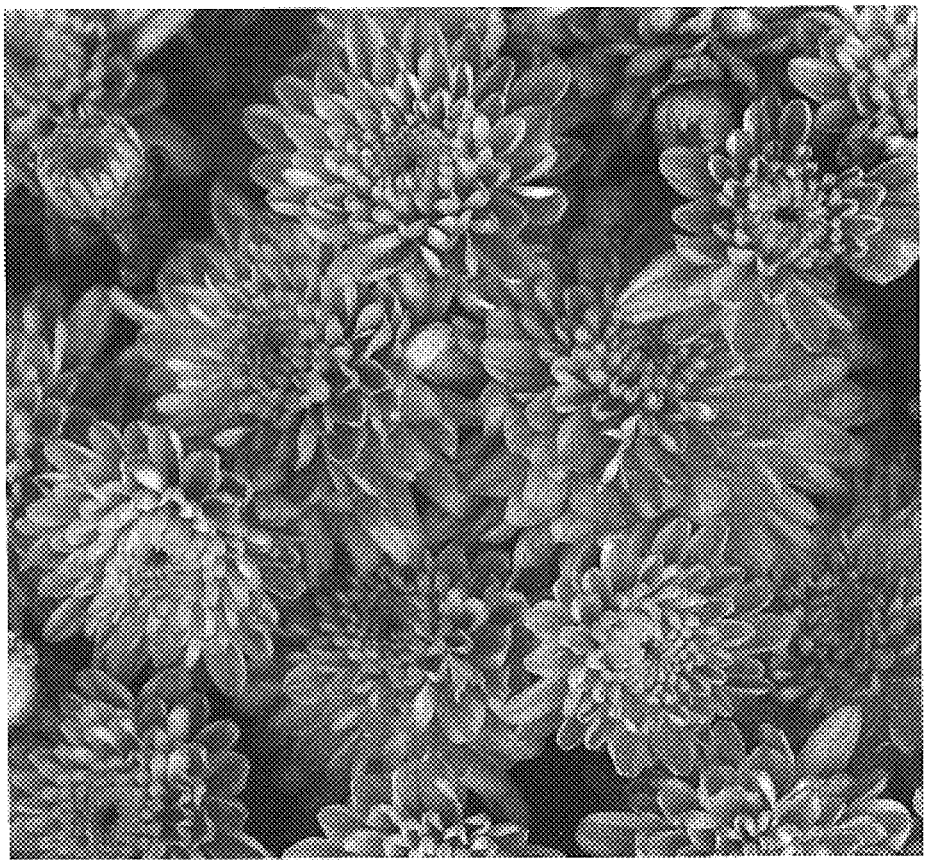

* * * * *